United States Patent
Shafer et al.

(10) Patent No.: US 12,023,006 B2
(45) Date of Patent: Jul. 2, 2024

(54) STEREOSCOPIC ENDOSCOPE

(71) Applicant: INTUITIVE SURGICAL OPERATIONS, INC., Sunnyvale, CA (US)

(72) Inventors: David C. Shafer, Menlo Park, CA (US); Dennis C. Leiner, Cape Elizabeth, ME (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 68 days.

(21) Appl. No.: 17/751,227

(22) Filed: May 23, 2022

(65) Prior Publication Data
US 2022/0280031 A1    Sep. 8, 2022

Related U.S. Application Data

(63) Continuation of application No. 16/051,592, filed on Aug. 1, 2018, now Pat. No. 11,382,496, which is a (Continued)

(51) Int. Cl.
*A61B 1/00* (2006.01)
*A61B 1/04* (2006.01)
(Continued)

(52) U.S. Cl.
CPC ...... *A61B 1/00193* (2013.01); *A61B 1/00045* (2013.01); *A61B 1/00194* (2022.02);
(Continued)

(58) Field of Classification Search
CPC ............ A61B 1/00193; A61B 1/00045; A61B 1/00194; A61B 1/000095; A61B 1/00096;
(Continued)

(56) References Cited

U.S. PATENT DOCUMENTS 3,499,107 A    3/1970  Sheldon
3,520,587 A    7/1970  Tasaki et al.
(Continued)

FOREIGN PATENT DOCUMENTS

WO    WO-199727798 A1    8/1997
WO    WO-2005032356 A1    4/2005
(Continued)

OTHER PUBLICATIONS

Blyth, Peter, "Converters Address Medical Equipment Compliance," Power Electronics Technology, Mar. 2006, pp. 38-41; Internet: www.powerelectronics.com.
(Continued)

*Primary Examiner* — Anh Tuan T Nguyen
*Assistant Examiner* — Shankar Raj Ghimire
(74) *Attorney, Agent, or Firm* — JONES ROBB, PLLC (57) ABSTRACT

A stereoscopic endoscope comprises a first lens train; a second lens train; a prism; and a continuous image sensor surface. The first lens train directs light along a first path through the first lens train and the prism to be incident on a first region of the continuous image sensor, and the second lens train directs light along a second path through the second lens train and the prism to be incident on a second region of the continuous image sensor.

20 Claims, 9 Drawing Sheets

Related U.S. Application Data continuation of application No. 14/341,098, filed on Jul. 25, 2014, now abandoned, which is a continuation of application No. 11/614,661, filed on Dec. 21, 2006, now Pat. No. 8,814,779.

(51) Int. Cl.
  *A61B 1/05* (2006.01)
  *G02B 5/04* (2006.01)
  *G02B 23/24* (2006.01)

(52) U.S. Cl.
  CPC .... *G02B 23/2415* (2013.01); *A61B 1/000095* (2022.02); *A61B 1/00096* (2013.01); *A61B 1/044* (2022.02); *A61B 1/05* (2013.01); *G02B 5/045* (2013.01)

(58) Field of Classification Search
  CPC ...... A61B 1/05; A61B 1/051; G02B 23/2415; G02B 5/045
  See application file for complete search history.

(56) References Cited

U.S. PATENT DOCUMENTS

| | | |
|---|---|---|
| 3,534,729 A | 10/1970 | Sakamoto |
| 3,788,303 A | 1/1974 | Hall et al. |
| 4,473,841 A | 9/1984 | Murakoshi et al. |
| 4,483,326 A | 11/1984 | Yamaka et al. |
| 4,491,865 A | 1/1985 | Danna et al. |
| 4,573,450 A | 3/1986 | Arakawa |
| 4,604,992 A | 8/1986 | Sato |
| 4,682,219 A | 7/1987 | Arakawa |
| 4,692,608 A | 9/1987 | Cooper et al. |
| 4,697,210 A | 9/1987 | Toyota et al. |
| 4,779,130 A | 10/1988 | Yabe |
| 4,779,613 A | 10/1988 | Hashiguchi et al. |
| 4,832,003 A | 5/1989 | Yabe |
| 4,834,069 A | 5/1989 | Umeda |
| 4,867,138 A | 9/1989 | Kubota et al. |
| 4,873,572 A | 10/1989 | Miyazaki et al. |
| 4,878,485 A | 11/1989 | Adair |
| 4,918,521 A | 4/1990 | Yabe et al. |
| 4,924,852 A | 5/1990 | Suzuki et al. |
| 4,924,853 A | 5/1990 | Jones, Jr. et al. |
| 5,051,823 A | 9/1991 | Cooper et al. |
| 5,051,824 A | 9/1991 | Nishigaki |
| RE33,854 E | 3/1992 | Adair |
| 5,096,292 A | 3/1992 | Sakamoto et al. |
| 5,122,650 A * | 6/1992 | McKinley .......... G02B 23/2415 359/362 |
| 5,124,838 A | 6/1992 | Forkey et al. |
| 5,166,787 A | 11/1992 | Irion |
| 5,188,094 A | 2/1993 | Adair |
| 5,191,203 A | 3/1993 | McKinley |
| 5,212,595 A | 5/1993 | Dennison, Jr. |
| 5,228,430 A | 7/1993 | Sakamoto |
| 5,237,446 A | 8/1993 | Takahashi |
| 5,299,559 A | 4/1994 | Bruce et al. |
| 5,305,121 A | 4/1994 | Moll |
| 5,349,137 A | 9/1994 | Cedrone |
| 5,377,669 A | 1/1995 | Schulz |
| 5,381,784 A | 1/1995 | Adair |
| 5,419,313 A | 5/1995 | Lemke |
| 5,430,475 A | 7/1995 | Goto et al. |
| 5,448,989 A | 9/1995 | Heckele |
| 5,454,827 A | 10/1995 | Aust et al. |
| 5,494,483 A | 2/1996 | Adair |
| 5,536,244 A | 7/1996 | Muller et al. |
| 5,557,454 A | 9/1996 | Takahashi |
| 5,577,991 A | 11/1996 | Akui et al. |
| 5,587,736 A | 12/1996 | Walls |
| 5,588,948 A | 12/1996 | Takahashi et al. |
| 5,599,278 A | 2/1997 | Hibbard |
| 5,603,687 A | 2/1997 | Hori et al. |
| 5,609,561 A | 3/1997 | Uehara et al. |
| 5,635,301 A | 6/1997 | Kondo et al. |
| 5,673,147 A | 9/1997 | McKinley |
| 5,743,846 A | 4/1998 | Takahashi et al. |
| 5,810,713 A | 9/1998 | Rondeau et al. |
| 5,835,133 A | 11/1998 | Moreton et al. |
| 5,841,126 A | 11/1998 | Fossum et al. |
| 5,860,912 A | 1/1999 | Chiba |
| 5,864,359 A | 1/1999 | Kazakevich |
| 5,868,664 A | 2/1999 | Speier et al. |
| 5,929,901 A | 7/1999 | Adair et al. |
| 5,940,126 A | 8/1999 | Kimura |
| 5,949,483 A | 9/1999 | Fossum et al. |
| 5,971,915 A | 10/1999 | Yamamoto et al. |
| 5,986,693 A | 11/1999 | Adair et al. |
| 5,990,469 A | 11/1999 | Bechtel et al. |
| 6,030,339 A | 2/2000 | Tatsuno et al. |
| 6,043,839 A | 3/2000 | Adair et al. |
| 6,063,023 A | 5/2000 | Sakiyama et al. |
| 6,080,101 A | 6/2000 | Tatsuno et al. |
| 6,104,426 A | 8/2000 | Street |
| 6,139,490 A * | 10/2000 | Breidenthal .......... H04N 13/161 348/E13.016 |
| 6,142,932 A | 11/2000 | Morizumi |
| 6,144,762 A | 11/2000 | Brooks |
| 6,146,326 A | 11/2000 | Pollack et al. |
| 6,149,582 A | 11/2000 | Morizumi |
| 6,166,768 A | 12/2000 | Fossum et al. |
| 6,191,809 B1 | 2/2001 | Hori et al. |
| 6,211,904 B1 | 4/2001 | Adair et al. |
| 6,223,100 B1 | 4/2001 | Green |
| 6,228,468 B1 | 5/2001 | Vodrahalli |
| 6,270,453 B1 | 8/2001 | Sakai |
| 6,275,255 B1 | 8/2001 | Adair et al. |
| 6,310,642 B1 | 10/2001 | Adair et al. |
| 6,328,691 B1 | 12/2001 | Rudischhauser |
| 6,390,972 B1 | 5/2002 | Speier et al. |
| 6,419,626 B1 | 7/2002 | Yoon |
| 6,424,369 B1 | 7/2002 | Adair et al. |
| 6,425,857 B1 | 7/2002 | Rudischhauser et al. |
| 6,436,107 B1 | 8/2002 | Wang et al. |
| 6,450,950 B2 | 9/2002 | Irion |
| 6,452,626 B1 | 9/2002 | Adair et al. |
| 6,471,642 B1 | 10/2002 | Igarashi |
| 6,503,196 B1 | 1/2003 | Kehr et al. |
| 6,547,722 B1 | 4/2003 | Higuma et al. |
| 6,558,316 B2 | 5/2003 | Kikuchi et al. |
| 6,572,536 B1 | 6/2003 | Bon et al. |
| 6,572,537 B2 | 6/2003 | Futatsugi et al. |
| 6,606,113 B2 | 8/2003 | Nakamura |
| 6,614,595 B2 | 9/2003 | Igarashi |
| 6,632,172 B1 | 10/2003 | Igarashi |
| 6,648,817 B2 | 11/2003 | Schara et al. |
| 6,692,430 B2 | 2/2004 | Adler |
| 6,692,431 B2 | 2/2004 | Kazakevich |
| 6,716,161 B2 | 4/2004 | Higuma et al. |
| 6,720,988 B1 | 4/2004 | Gere et al. |
| 6,721,008 B2 | 4/2004 | Lee et al. |
| 6,767,322 B1 | 7/2004 | Futatsugi et al. |
| 6,817,974 B2 | 11/2004 | Cooper et al. |
| 6,817,975 B1 | 11/2004 | Farr et al. |
| 6,862,036 B2 | 3/2005 | Adair et al. |
| 6,891,266 B2 | 5/2005 | Kinayman et al. |
| 6,898,022 B2 | 5/2005 | Igarashi |
| 6,932,760 B1 | 8/2005 | Pang et al. |
| 6,955,644 B2 | 10/2005 | Forkey et al. |
| 6,976,956 B2 | 12/2005 | Takahashi et al. |
| 6,982,740 B2 | 1/2006 | Adair et al. |
| 6,982,742 B2 | 1/2006 | Adair et al. |
| 7,030,904 B2 | 4/2006 | Adair et al. |
| 7,046,270 B2 | 5/2006 | Murata et al. |
| 7,074,181 B2 | 7/2006 | Futatsugi |
| 7,170,677 B1 | 1/2007 | Bendall et al. |
| 7,410,462 B2 | 8/2008 | Navok et al. |
| 7,852,371 B2 | 12/2010 | Konstorum et al. |
| 8,144,409 B2 | 3/2012 | Lin et al. |
| 8,219,178 B2 | 7/2012 | Smith et al. |
| 8,556,807 B2 | 10/2013 | Scott et al. |
| 8,602,967 B2 | 12/2013 | Robertson |

(56) References Cited

U.S. PATENT DOCUMENTS

| | | |
|---|---|---|
| 8,633,975 B2 | 1/2014 | Amling |
| 8,723,922 B2 | 5/2014 | Berger |
| 8,814,779 B2 | 8/2014 | Shafer et al. |
| 8,974,472 B2 | 3/2015 | Gal et al. |
| 9,005,113 B2 | 4/2015 | Scott et al. |
| 9,118,850 B2 | 8/2015 | Luo et al. |
| 9,196,176 B2 | 11/2015 | Hager et al. |
| 9,271,633 B2 | 3/2016 | Scott et al. |
| 9,486,189 B2 | 11/2016 | Oko et al. |
| 9,565,997 B2 | 2/2017 | Scott et al. |
| 9,621,825 B2 | 4/2017 | Luo et al. |
| 9,699,445 B2 | 7/2017 | Hoffman et al. |
| 9,829,697 B2 | 11/2017 | Zobel |
| 9,835,821 B1 | 12/2017 | Yin et al. |
| 9,962,069 B2 | 5/2018 | Scott et al. |
| 9,965,856 B2 | 5/2018 | Weiss |
| 10,084,944 B2 | 9/2018 | Henley et al. |
| 10,136,954 B2 | 11/2018 | Johnson et al. |
| 10,188,411 B2 | 1/2019 | Bonneau et al. |
| 10,219,864 B2 | 3/2019 | Bonneau et al. |
| 10,231,791 B2 | 3/2019 | Leboeuf, II et al. |
| 10,682,046 B2 | 6/2020 | Scott et al. |
| 11,039,738 B2 | 6/2021 | Scott et al. |
| 11,382,496 B2 | 7/2022 | Shafer et al. |
| 2001/0012053 A1* | 8/2001 | Nakamura ......... A61B 1/00193 348/45 |
| 2001/0017649 A1 | 8/2001 | Yaron |
| 2001/0033326 A1 | 10/2001 | Goldstein et al. |
| 2002/0021354 A1 | 2/2002 | Suzuki et al. |
| 2002/0072653 A1 | 6/2002 | Ishizuka |
| 2002/0154215 A1 | 10/2002 | Schechterman et al. |
| 2002/0183590 A1 | 12/2002 | Ogawa |
| 2003/0004399 A1 | 1/2003 | Belson |
| 2003/0125608 A1 | 7/2003 | Igarashi |
| 2003/0215608 A1 | 11/2003 | Bermel |
| 2003/0233024 A1 | 12/2003 | Ando |
| 2004/0082833 A1 | 4/2004 | Adler et al. |
| 2005/0023356 A1 | 2/2005 | Wiklof et al. |
| 2005/0267328 A1 | 12/2005 | Blumzvig et al. |
| 2006/0025655 A1 | 2/2006 | Uram |
| 2006/0069314 A1 | 3/2006 | Farr |
| 2006/0076472 A1 | 4/2006 | Dosluoglu et al. |
| 2006/0178559 A1 | 8/2006 | Kumar et al. |
| 2006/0183976 A1 | 8/2006 | Adler et al. |
| 2007/0073109 A1 | 3/2007 | Irion |
| 2007/0106119 A1 | 5/2007 | Hirata et al. |
| 2007/0156285 A1 | 7/2007 | Sillman et al. |
| 2007/0232860 A1 | 10/2007 | Kubo et al. |
| 2007/0255100 A1 | 11/2007 | Barlow et al. |
| 2008/0065105 A1 | 3/2008 | Larkin et al. |
| 2008/0185603 A1 | 8/2008 | Itoi et al. |
| 2008/0208006 A1 | 8/2008 | Farr |
| 2008/0287963 A1 | 11/2008 | Rogers et al. |
| 2008/0300463 A1 | 12/2008 | Navok et al. |
| 2009/0076329 A1 | 3/2009 | Su et al. |
| 2009/0096865 A1 | 4/2009 | McKinley |
| 2009/0245600 A1 | 10/2009 | Hoffman et al. |
| 2009/0248036 A1 | 10/2009 | Hoffman et al. |
| 2010/0168918 A1 | 7/2010 | Zhao et al. |
| 2010/0169815 A1 | 7/2010 | Zhao et al. |
| 2010/0261961 A1* | 10/2010 | Scott .................. A61B 1/00165 600/111 |
| 2010/0317965 A1 | 12/2010 | Itkowitz et al. |
| 2010/0318099 A1 | 12/2010 | Itkowitz et al. |
| 2010/0331855 A1 | 12/2010 | Zhao et al. |
| 2011/0009880 A1 | 1/2011 | Prisco et al. |
| 2011/0034769 A1 | 2/2011 | Adair et al. |
| 2011/0043612 A1 | 2/2011 | Keller et al. |
| 2011/0071347 A1 | 3/2011 | Rogers et al. |
| 2011/0071541 A1 | 3/2011 | Prisco et al. |
| 2011/0071543 A1 | 3/2011 | Prisco et al. |
| 2011/0071544 A1 | 3/2011 | Steger et al. |
| 2011/0115882 A1 | 5/2011 | Shahinian et al. |
| 2012/0209288 A1 | 8/2012 | Robinson |
| 2013/0250061 A1 | 9/2013 | Hofer |
| 2014/0236177 A1 | 8/2014 | Verner et al. |
| 2014/0253684 A1 | 9/2014 | Kumar et al. |
| 2014/0277738 A1 | 9/2014 | Diolaiti et al. |
| 2014/0336460 A1 | 11/2014 | Shafer et al. |
| 2014/0343569 A1 | 11/2014 | Turner |
| 2016/0166339 A1 | 6/2016 | Labonville et al. |
| 2017/0000575 A1 | 1/2017 | Griffiths et al. |
| 2017/0172675 A1 | 6/2017 | Jarc et al. |
| 2017/0180720 A1 | 6/2017 | Jarc |
| 2018/0064318 A1 | 3/2018 | Kitano |
| 2018/0206925 A1 | 7/2018 | Radel et al. |
| 2019/0029501 A1 | 1/2019 | Shafer et al. |
| 2019/0216554 A1 | 7/2019 | Kapadia |
| 2021/0378497 A1 | 12/2021 | Scott et al. |

FOREIGN PATENT DOCUMENTS

| | | |
|---|---|---|
| WO | WO-2013059821 A2 | 4/2013 |
| WO | WO-2014144947 A1 | 9/2014 |
| WO | WO-2014144986 A1 | 9/2014 |
| WO | WO-2015126466 A1 | 8/2015 |
| WO | WO-2015163942 A1 | 10/2015 |

OTHER PUBLICATIONS

Dogangil G., et al., "A Review of Medical Robotics for Minimally Invasive Soft Tissue Surgery," Proceedings of the Institution of Mechanical Engineers. Part H, Journal of Engineering in Medicine, May 2009, vol. 224 (5), pp. 653-679.

Horise Y., et al., "Development of a Locally-operated Master Device and a Flexible Slave Robot System for Single-incision Laparoscopic Surgery," International Journal of Computer Assisted Radiology and Surgery, Jun. 2014, vol. 9 (Suppl 1), pp. S141-S163.

International Search Report for Application No. PCT/US12/61375, dated Mar. 14, 2013, 4 pages.

PCT/US07/85714 International Search Report and Written Opinion of the International Searching Authority, dated Jul. 2, 2008, 10 pages.

Powervar, Inc., "IEC 601: What Are the Implications for Power Quality" White Paper # 211, 2002, 10 pages.

Schurr M.O., "Robotics and Systems Technology for Advanced Endoscopic Procedures: Experiences in General Surgery," European Journal of Cardio-thoracic Surgery, Nov. 1999, vol. 16 (Suppl 2), pp. S97-S105.

Sidebottom, Charles et al., IEC 60601-1, Third Edition, The Journal of Medical Device Regulation, May 2006, pp. 8-17.

Techneglas, Inc., "FRIT FACTS: A Brief Technological Summary of Television Solder Glass for CRT Technicians,Engineers and Managers," posted online Mar. 25, 2006, 40 pages, Internet: http://www.techneglas.com/products/frit.pdf.

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

Wang L., et al., "Miniaturized, CMOS Imaging Module with Real-time DSP Technology for Endoscope and Laryngoscope Applications," Journal of Signal Processing Systems, 2009, vol. 54 (1-3), pp. 7-13.

Written Opinion for Application No. PCT/US12/61375, dated Mar. 14, 2013, 6 pages.

* cited by examiner

STEREOSCOPIC ENDOSCOPE

CROSS REFERENCE TO RELATED APPLICATIONS

This application is a continuation of U.S. application Ser. No. 16/051,592, filed Aug. 1, 2018, which is a continuation of U.S. application Ser. No. 14/341,098, filed Jul. 25, 2014 (now abandoned), which is a continuation of U.S. application Ser. No. 11/614,661, filed Dec. 21, 2006 (now U.S. Pat. No. 8,814,779), each of which is incorporated by reference herein in its entirety.

BACKGROUND

1. Field of Invention

The invention pertains to stereoscopic imaging systems, and more particularly to stereoscopic image capture endoscopes.

2. Background Art

The field of minimally invasive surgery (e.g., laparoscopic surgery) requires increasingly smaller, increasingly mobile stereoscopic imaging systems. Stereoscopic endoscopes are typically mounted at the distal end of rigid shafts that extend through a cannula so as to image a surgical site during, e.g., robot-assisted surgery.

To get acceptable stereoscopic imaging without causing viewer fatigue or eyestrain, the images of the target object viewed by the two imaging systems should match in at least the following alignment parameters: (1) image location along the horizontal axis; (2) image location along the vertical axis; (3) image rotation; (4) image scale; (5) geometric distortion; (5) focus at the image center; (6) focal shift along the horizontal axis; and (7) focal shift along the vertical axis. The tolerable errors in the matching between the two images in a stereoscopic pair depend to some extent upon the display and viewer, but in general are much more stringent requirements than exist for monocular viewing. In addition, except for the image location, mismatches in the other parameters are difficult to correct for in image post-processing without introducing imaging artifacts.

While these parameters are all affected to some degree by the positions of the optical elements in the imaging system, they are also affected by the accuracy of the mounting of the two image sensors conventionally used in a stereoscopic endoscope with respect to each other. Taking one of the sensors as a reference, the position of a second, separate, sensor has six degrees of freedom in its mounting: three of translation and three of rotation. Errors in two of the translation axes between the sensors affect the relative horizontal and vertical positions of the viewed images, while errors in the third translation axis, the axis perpendicular to the sensor surface, affects both the image scale (if the objective is not telecentric in image space) and focus. Errors in rotation between the two image sensors, around the axis perpendicular to the sensor surface, directly affect image rotation and cannot always be corrected by alignment of the optics, while rotation errors about the other two axes affect the focal plane shifts across the imaging field.

In three dimensions, a rigid body (e.g., an optical image sensor chip) has six degrees of freedom: moving up and down (heaving), moving left and right (swaying), moving forward and backward (surging), tilting up and down (pitching), turning left and right (yawing), and tilting side to side (rolling). With two separate image sensors there are a total of 12 degrees of freedom that must be controlled when mounting the two sensors to the optical train. For example, if two physically separate sensors are used, then each sensor must be aligned with its respective optical train and additional image processing (e.g., to compensate for rotation) is required in order to align the captured left and right images with each other to present the stereoscopic view to a person viewing the images.

SUMMARY

In aspects of the invention, two side-by-side optical paths transmit stereoscopic right side and left side images onto the surface of a single image sensing chip. The single image sensing chip may be placed at various orientations (e.g., perpendicular, parallel) with respect to the lens trains in the optical paths.

In some aspects of the invention, a single prism is used to turn the light for both the right side and left side images onto the single image sensing chip.

In other aspects of the invention, one prism is used to turn the light for the right side image and another prism is used to turn the light for the left side image, and the reflective surfaces of the two prisms are substantially coplanar such that the right side and left side images are incident on the single image sensor chip.

DETAILED DESCRIPTION

In the following description, reference is made to the accompanying drawings, which illustrate embodiments of the invention. It is understood that other embodiments may be used, and mechanical, compositional, structural, electrical, and operational changes may be made, without departing from the spirit and scope of this disclosure. The following detailed description is not to be taken in a limiting sense. The scope of the embodiments of the invention is defined only by the claims of the issued patent.

The terminology used in this description is to describe particular embodiments only and is not intended to limit the invention. Spatially relative terms, such as "beneath", "below", "lower", "above", "upper", "underlying", "outside", "between", and the like may be used to describe one element's or feature's relationship to another as illustrated in the figures. The spatially relative terms are for ease of description and are intended to encompass different orientations of the device in use or operation in addition to the orientation shown in the figures. For example, if the device in the figures is turned over, elements described as "below" or "beneath" other elements or features would then appear to be oriented "above" the other elements or features. Nevertheless, the exemplary term "below" can encompass a real world orientation of above and below. The device may be otherwise oriented (e.g., rotated 90 degrees or other orientations) and the spatially relative descriptors used in this description should be interpreted accordingly.

As used in this description, the singular forms "a", "an", and "the" are intended to include the plural forms as well, unless the context indicates otherwise. The terms "comprises" and/or "comprising", "includes" and/or "including", and the like specify the presence of stated features, steps, operations, elements, and/or components, but do not preclude the presence or addition of one or more other features, steps, operations, elements, components, and/or groups.

Numerous specific details are described to provide a thorough understanding of the present invention. In certain instances, however, well known or conventional details are not described in order to avoid obscuring the description of the present invention. References to one or an embodiment in this disclosure are not necessarily to the same embodiment, and such references mean at least one. Like numbers in the drawings refer to the same or similar elements.

Consider an image sensor positioned flat with reference to the ground (two horizontal axes at 90 degrees with respect to each other, and a vertical axis). If this single, larger image sensor is used to record the images from the two side by side stereoscopic optical trains, only 6 degrees of freedom exist in mounting the sensor with reference to the optical trains as opposed to 12 if two separate sensors are used. Furthermore, of these 6 degrees of freedom, the three translational degrees (heaving, swaying, surging) cause imaging errors that affect both the right and the left side images in an equal way, which maintains good stereoscopic viewing. Rotation around the axis perpendicular to the sensor surface (yawing) requires cropping off a small amount of the field along the edges, but both images rotate by exactly the same amount. In addition, although the entire image appears slightly rotated, the two views do not experience any differential rotation, to which the viewer is much more sensitive. Tilt of the sensor around an axis oriented horizontally (pitching) causes tilt of the focal plane, but again to the same degree in both images. The final axis, which is tilt of the sensor about the other horizontal axis (rolling), does affect the two images differentially, but an optical adjustment may be made to correct for this by moving one of the optical trains back and forth to match the focus point of the other optical train.

Figure 1:
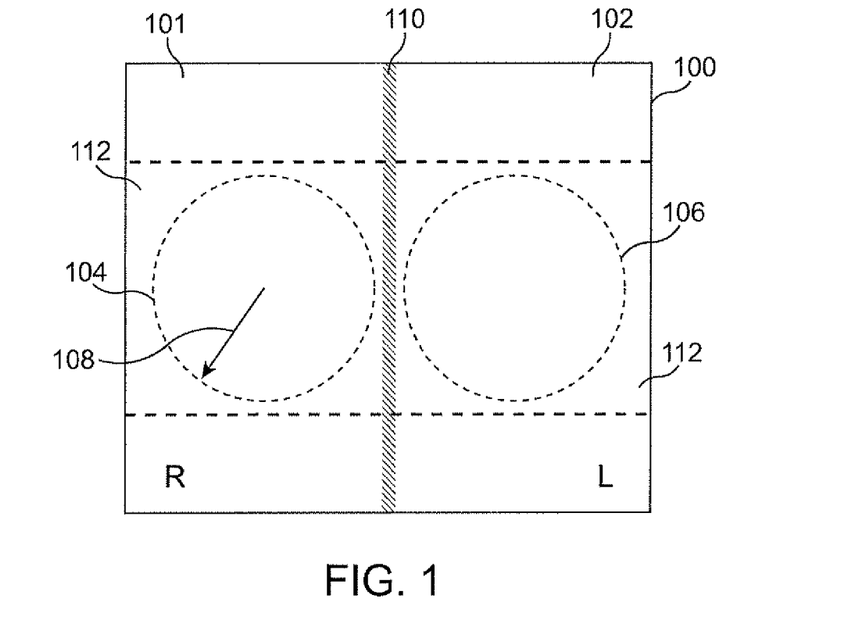
FIG. 1 is an illustrative, diagrammatic plan view of the active image sensing area of an image sensing semiconductor integrated circuit.

FIG. 1 is an illustrative, diagrammatic plan view of the active image sensing area 100 of an image sensing semiconductor integrated circuit (e.g., CCD, CMOS). Additional active circuits and packaging are omitted from the drawing for clarity. In one embodiment, the width:height dimensional aspect ratio of image sensing area 100 is approximately 5:4 (Micron Technology, Inc. MT9M131). In other embodiments, other standard aspect ratios such as 4:3 or 16:9 may be used. In still other embodiments, a custom sized image sensing area may be fabricated to eliminate portions of the sensing area that are not used to capture images. Such custom sizing helps save space in small endoscope distal ends. Such custom sizing may also accommodate desired optical configurations for desired stereoscopic viewing, as described in detail below.

Two optical paths, described below, cause stereoscopic images to be incident on the surface of image sensing area 100. The right side image 101 is incident on one side of image sensing area 100. Likewise, the left side image 102 is incident on the other side of image sensing area 100. Skilled artisans will understand that various optical train configurations may cause the right and left side images 101,102 to be incident on either side of image sensing area 100. As described above and in more detail below, the use of a single, planar substrate for sensing stereoscopic images makes alignment during construction easier and the imaging device more compact than if two physically separate image sensor chips are used.

With a single, planar substrate some image processing may be required to move the right and left images up or down with respect to each other so as to correct for position errors of the optical trains with respect to the sensor surface, but processing for rotation or scaling is not necessary, and the focal planes of the two images are automatically in alignment. By using a single sensor to record both images of a stereoscopic pair, the problems of alignment in manufacture are greatly simplified, and the resulting imaging system is simpler and more resistant to misalignment due to shocks, thermal cycles, and other effects occurring over the image capture system's (e.g., endoscope's) lifetime.

The optics in the optical paths are configured to provide a minimally distorted image within a particular circular area. As shown in FIG. 1, this particular area is represented by the dashed line circle areas 104 for the right side image 101 and 106 for the left side image 102. In one embodiment the optimized area is an approximately 25-degree radius from the center of the image, as represented by radius arrow 108 in FIG. 1. Other embodiments may optimize images for other fields of view, as measured on the diagonal at a viewing system, or optimize over an image area of non-circular shape. Image information outside the optimized areas 104,106 is usable despite being of slightly less optical quality.

Also shown in FIG. 1 is an image cross-talk region 110 between the right and left side images 101,102 that are incident on image sensing area 100. As described in more detail below, one or more field separators and/or field stops prevent most of the right side image 101 from being incident on the side of image sensing area 100 that receives the left side image 102, and vice versa. A small amount of image cross-talk does exist, however, and so the optical paths position circle areas 104,106 with some space between them to avoid being in cross-talk region 110.

In the embodiment depicted in FIG. 1, only a horizontal portion 112 that includes circle areas 104 and 106, shown between the two heavy dashed lines, of image sensing area 100 is read during each image frame capture. Areas generally above and below circle areas 104,106 are not read out since the image data in these areas will not be used in the image display. This limited read out of data helps speed image capture and processing time. Consequently, frame rate may be increased above the rate required if all of image sensing area 100 data were read. One embodiment uses a 24-30 fps progressive scan. Other embodiments may use higher rate, e.g., 60 Hz, progressive or interlaced scanning. Alternatively, or in combination with the increased frame rate, image sensing area 100 may have a higher pixel pitch (number of pixels per unit area) since unusable image data is not being read out and sent to downstream image processing circuits. A custom sized image sensing area 100 may be fabricated to match the dimensions of horizontal portion 112. The size and position of circle areas 104,106 are determined by design considerations described below.

Figure 2:
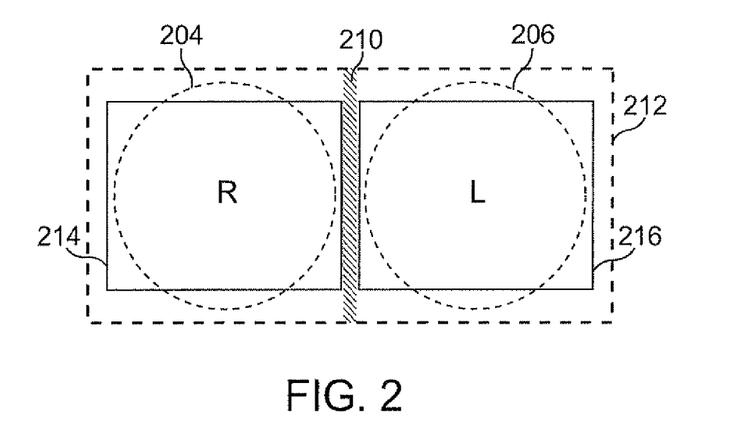
FIG. 2 is a diagrammatic view of image data that is captured by an image sensor.

FIG. 2 is a diagrammatic view of image data that is captured by image sensing area 100. Data 212 corresponds to data captured by horizontal portion 112. Right optimum image data in circle 204 corresponds to the optimum image data captured in circle area 104, and left optimum image data in circle 206 corresponds to the optimum image data captured in circle area 106. Cross-talk data 210 corresponds to image data captured in cross-talk region 110. As described below, in some cases the captured image data is stored in a memory for subsequent image processing.

FIG. 2 shows two illustrative display image data areas 214,216. The data used for displaying the right side image is in display image data area 214. Similarly, the data used for displaying the left side image is in display image data area 216. As shown in FIG. 2, display image data areas 214,216 are rectangular with an approximately 4:3 width:height aspect ratio, which corresponds to the width:height aspect ratio of the displays (e.g., CRTs) used to output the images in one embodiment. In other embodiments, display image data areas 214,216 have different aspect ratios such as, e.g., 16:9 or 1:1, which may or may not correspond to the width:height aspect ratio of the output displays, depending on the desired stereoscopic image for viewing. In still other embodiments, display image data areas 214,216 are non-rectangular (e.g., circular, octagonal, etc.). As shown in FIG. 2, in order to capture most of the optimum right and left image data, a small amount of non-optimum image data exists at the corners of rectangular display image data areas 214,216. Display image data areas 214,216 are defined to not include cross-talk data 210. The data in display image data areas 214,216 of data 212 are further processed using well-known image data processing methods.

Figure 3:
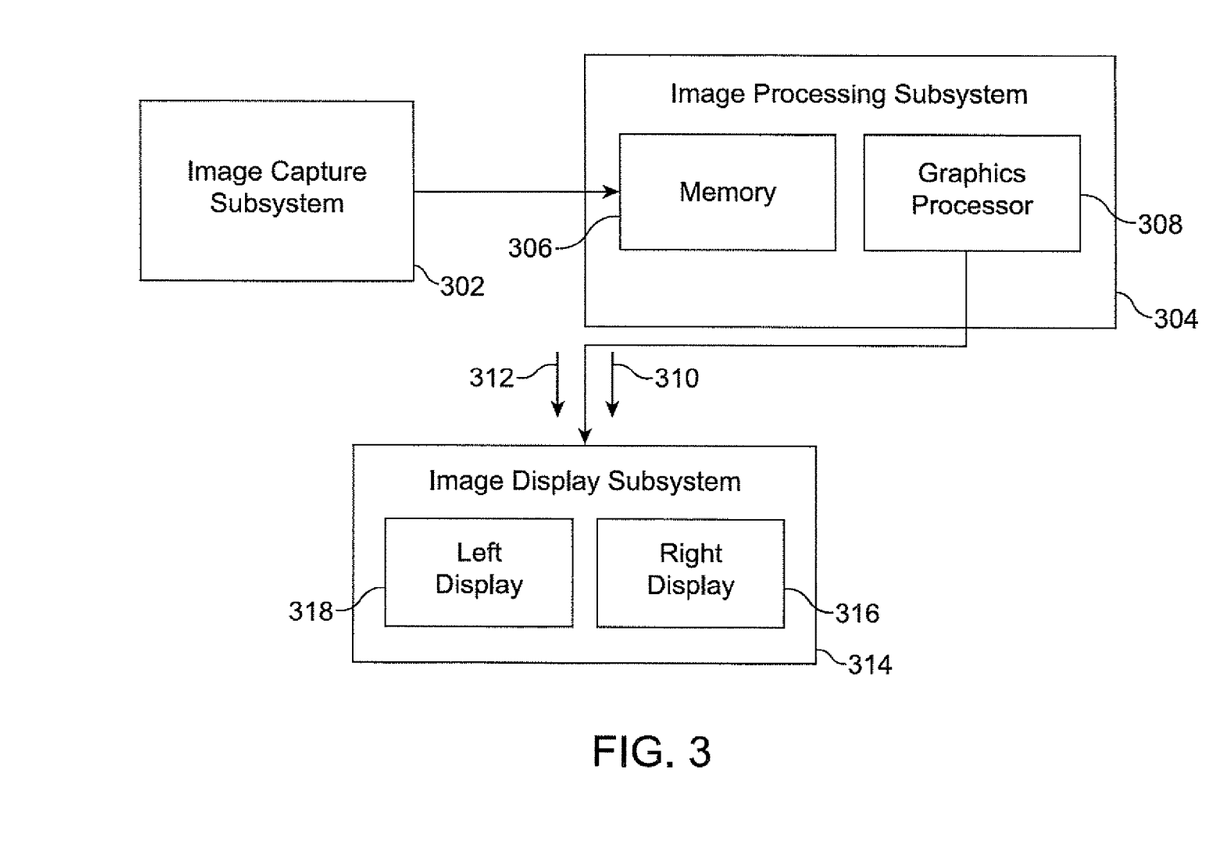
FIG. 3 is a diagrammatic view of a stereoscopic imaging and viewing system.

FIG. 3 is a diagrammatic view of a stereoscopic imaging system. Image capture subsystem 302, described in more detail below, captures stereoscopic image data as described above with reference to FIG. 1. Image processing subsystem 304 includes memory 306 and graphics processor 308. Memory 306 stores captured image data as described above with reference to FIG. 2. Right and left display image data (formatted as, e.g., S-Video, VGA, DVI, SDI and shown as representative arrows 310,312) are sent from graphics processor 308 to image display subsystem 314. In one embodiment image processing subsystem 304 is a personal computer, and graphics processor 308 is a dual-head graphics processing card. In another embodiment, image processing subsystem 304 is an image processing system that is dedicated for use in a surgical operating room. Because the right and left images in the stereoscopic pair are read out of the sensor together, the scanning of the two images is inherently synchronized, and therefore the image processing subsystem 304 can be designed to operate on the images in a flow-through fashion, without requiring the storage of a full frame of image data in memory 306. This flow-through design minimizes the latency in the presentation of the stereoscopic image to the viewer, which is important in many applications and is not possible if the scanning of the right and left images is not synchronized.

Image display subsystem 314 includes right display 316 and left display 318. Optics (not shown) allow the viewer to simultaneously view displays 316,318 and perceive a stereoscopic image. In one embodiment image display subsystem 314 is the surgeon's console on an Advance® surgical robotic system manufactured by Intuitive Surgical, Inc. of Sunnyvale, Calif., which displays the stereo image at about an 18-inch working distance.

Figure 4:
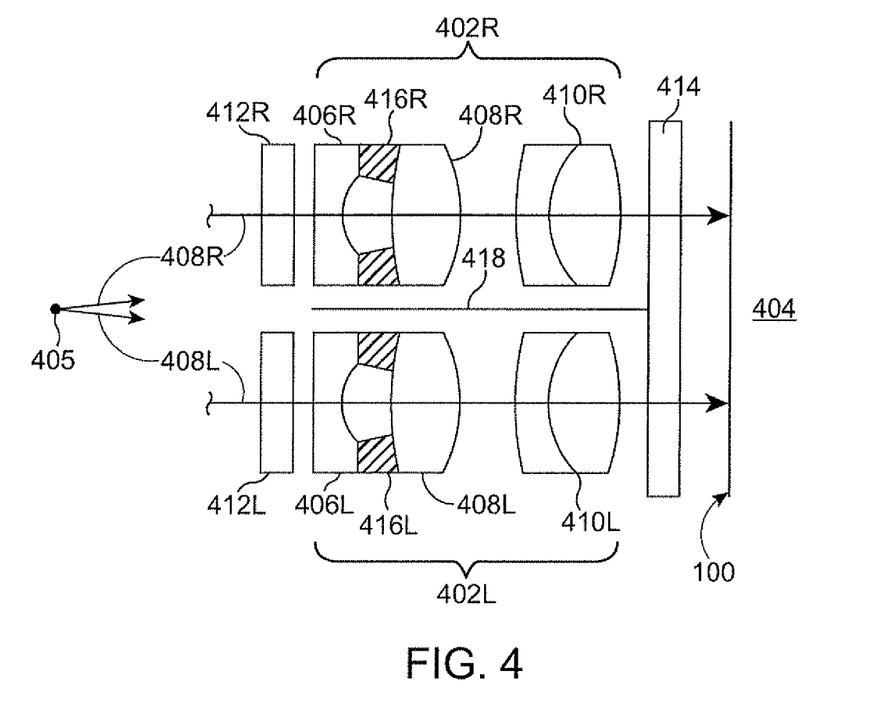
FIG. 4 is a schematic plan view of imaging optics.

FIG. 4 is an illustrative, schematic plan view of an embodiment of imaging optics used in image capture subsystem 302. FIG. 4 shows two parallel optical lens trains 402R and 402L positioned side-by-side in front of an imaging integrated circuit 404. Light (e.g., visible, infrared, ultraviolet), shown in FIG. 4 as ray 408R for the right side image and as ray 408L for the left side image, from object 405 passes through the two lens trains 402R,402L and is incident on image sensing area 100 of imaging integrated circuit 404, as described above. As shown in FIG. 4, in one embodiment rays 408R and 408L pass from object 405 to image capture area 100 without turning. The optical paths from object 405 to image capture area 100 do not include any turns other than the refraction from the lenses, filter, and windows.

Right lens train 402R includes objective negative lens 406R, positive lens 408R positioned behind lens 406R, and doublet 410R positioned behind lens 408R. Left lens train 402L includes similar counterpart lenses 406L, 408L, and 410L. The lenses shown in FIG. 4 are illustrative of various lens configurations that may be used in the optical trains. In one embodiment lenses 406R, 408R, and 410R are held in position within a tube (not shown) so that the entire lens train can be moved for focusing, and left lens train 402L is similarly configured.

In addition to the lenses, FIG. 4 shows various other components of this embodiment of image capture subsystem 302. Window 412R is shown positioned in front of lens 406R, and window 412L is shown positioned in front of lens 406L. In other embodiments a single window may be used. The window or windows are made from, e.g., sapphire and protect the lenses. Also shown in FIG. 4 is infrared (IR) filter (color balancing filter) 414 positioned between lenses 410R, 410L and image capture area 100. In other embodiments separate IR filters may be used for each lens train. The IR filter or filters may be at other positions along the optical path between object 406 and image sensor area 100. FIG. 4 further shows illustrative aperture stop 416R positioned between lens 406R and lens 408R. Likewise, aperture stop 416L is shown positioned between lens 406L and 408L. The aperture stop positions are illustrative of various positions. In one embodiment aperture stops 416R,416L have fixed apertures, and in other embodiments the apertures may be variable. Finally, FIG. 4 shows illustrative field separator 418 positioned between right and left lens trains 402R,402L. Field separator 418 is made of non-reflective material and helps eliminate image cross talk at image sensor area 100. As shown, field separator 418 stops at IR filter 414. In other embodiments, illustrated below, field separator 418 may extend closer to image sensor area 100. The tubes surrounding and holding the right and left lens trains 402R,402L may function as field separator 418, and/or field separator 418 may include other structures.

Since object 405 is a finite distance from lenses 412R and 412L, persons skilled in the art will understand that the distance between the centers of the right side and left side images on the surface 100 of imaging integrated circuit 404 is slightly more than the interpupillary distance between lenses 412R and 412L. Thus it can be seen that in embodiments of the invention the stereoscopic right and left side optical paths are spaced apart generally on the scale of the image sensor chip upon which the right and left side images are incident.

Figure 5:
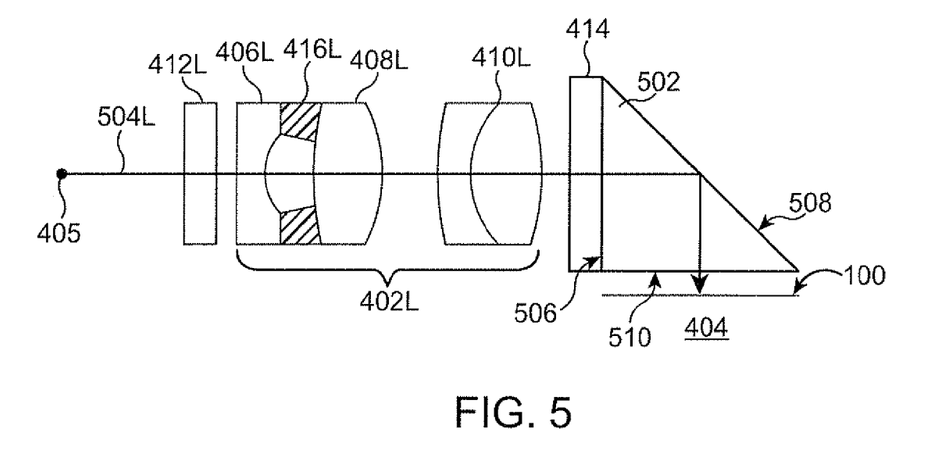
FIG. 5 is a schematic side elevation view of imaging optics.

FIG. 5 is a schematic side elevation view of another embodiment of imaging optics used in image capture subsystem 302. As shown in FIG. 5, the configuration of the imaging optics is similar to the configuration shown in FIG. 4, but the optical path between object 405 and image capture area 100 is turned once by reflective prism 502. Lens train 402L is shown in FIG. 5. Lens train 402R is directly behind and obscured by lens train 402L in this view.

As shown in FIG. 5, left side image ray 504L passes through window 412L, through optical train 402L, and through IR filter 414 in a manner similar to that described for FIG. 4. After exiting IR filter 414, however, left side image ray 504L passes through side face 506 of prism 502, is internally reflected by side face 508, and then exits side face 510 to be incident on image capture area 100. A counterpart right side image ray (not shown) similarly passes through lens train 402R, is turned by prism 502, and is incident on image capture area 100. Prism 502 is a single prism that turns both the right side and the left side images, as described in more detail below. Thus side face 508 acts as a single reflective plane for both the right and left side images of object 405. As a consequence of this reflection, the image will be inverted on the sensor with respect to the image formed by the optical train shown in FIG. 4. The image can be displayed correctly on the display by inverting it in image processing subsystem 304 (FIG. 3), or preferably by altering the scanning pattern of image sensor 404 to match the inverted image, which avoids the processing delay associated with performing the inversion after scanning.

In one embodiment, illustrated by FIG. 5, IR filter 414 is coupled directly to side face 506 of prism 502. In other embodiments, IR filter 414 may be at various other positions.

Since the plane of image capture area 100 is shown as being substantially perpendicular to rays 408R,408L in FIG. 4, the associated integrated circuit 404 occupies a relatively large cross-sectional area compared to the cross-sectional area of the optical trains. Accordingly, the cross-sectional area of image capture subsystem 302 is relatively large so as to accommodate integrated circuit 404 and its associated hardware and electronic interface circuitry. Turning the optical paths as shown in FIG. 5 allows integrated circuit 404 to be positioned so that the plane of sensor area 100 is substantially parallel to rays 408R,408L passing through the optical trains. Consequently, the cross-sectional area of image capture subsystem 302 is relatively smaller. Prism 502 is shown as a right isosceles triangular prism, although in other embodiments other prism configurations can be used. In addition, the plane of sensor area 100 may be tilted from the substantially parallel position illustrated in FIG. 5.

FIG. 5 illustrates embodiments in which object 405 is generally directly in line with the longitudinal axes of lens trains 402R,402L. In other embodiments, in order to give the image capture system an upward, downward, or sideward viewing angle, one or more reflecting prisms or other optical components can be placed, e.g., between windows 412R, 412L and objective lenses 406R,406L in accordance with well-known optical design principles.

Figure 6:
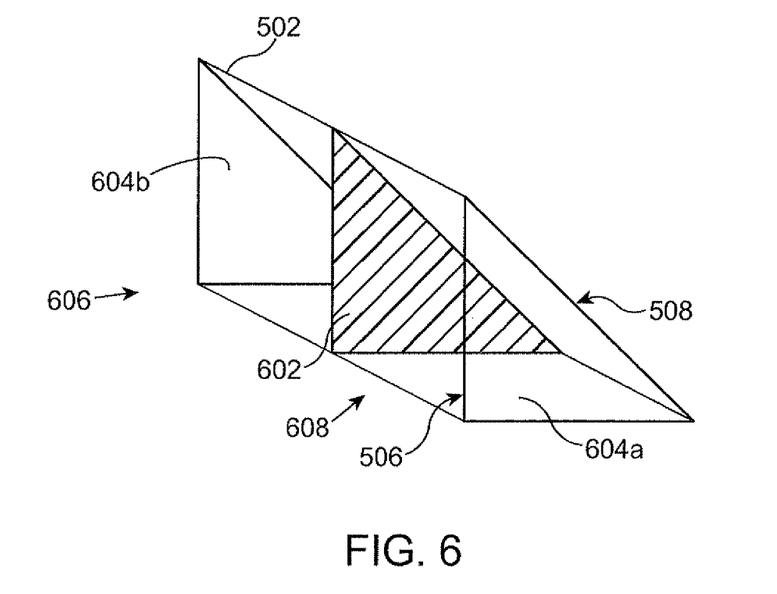
FIG. 6 is a perspective view of a prism.

FIG. 6 is a perspective view showing details of one embodiment of prism 502. As shown in FIG. 6, prism 502 is a single prism that includes field separator 602 half-way between the two base faces 604a,604b. The right half 606 of prism 502 reflects the right side image, and the left half 608 of prism 502 reflects the left side image. Field separator 602 prevents light from the right and left side images from crossing into the sensor areas for the opposite side image. Field separator 602 is a non-reflective coating. In one embodiment, the non-reflective coating is applied to the material (e.g., glass) used for one half of prism 502, and then the material used for the other half of prism 502 is attached to the first half so that the non-reflective coating is between the two halves. Then, prism 502 is ground and polished as a single prism having a field separator sandwiched between the two halves. Since prism 502 is a single prism having a single side face 508 that is used to reflect both right and left images in the stereoscopic system, alignment operations with the underlying image capture area 100 and the right and left lens trains are made easier than if, e.g., two separate prisms were to be used. It can be seen that side face 508 internally reflects both right and left images onto the underlying image capture area 100. In an alternative embodiment, prism 502 may be composed of two separate parts, each of which has the field separator 602 applied, and the two parts may be aligned at the time the lenses are mounted.

Figure 7:
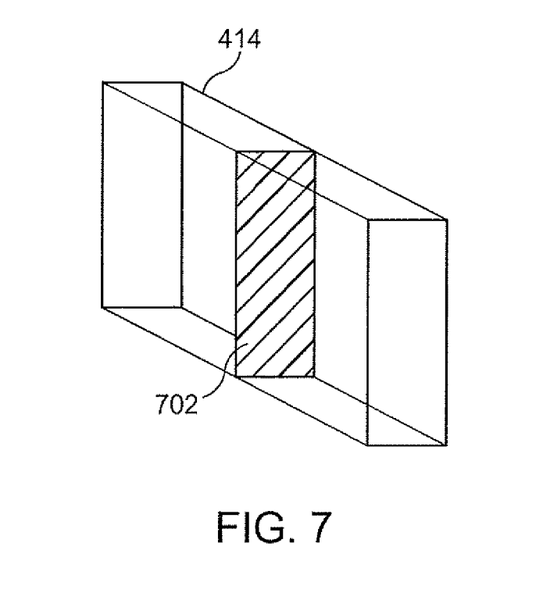
FIG. 7 is a perspective view of an infrared filter.

FIG. 7 is a perspective view showing details of one embodiment of IR filter 414. In the embodiment illustrated by FIG. 7, IR filter 414 is a rectangular prism configured with a field separator 702 in a manner similar to the embodiment of prism 502 illustrated by FIG. 6. In other embodiments in which separate IR filters are used for each right and left side image, a separate field separator may be used between the two filters. In still other embodiments in which the IR filter is very thin, the field separator may be eliminated. In some embodiments the IR filter or filter is glued to the end of tubes holding the lens train, as described below. In some embodiments the IR filter or filters are glued to side face 506 of prism 502.

Figure 8:
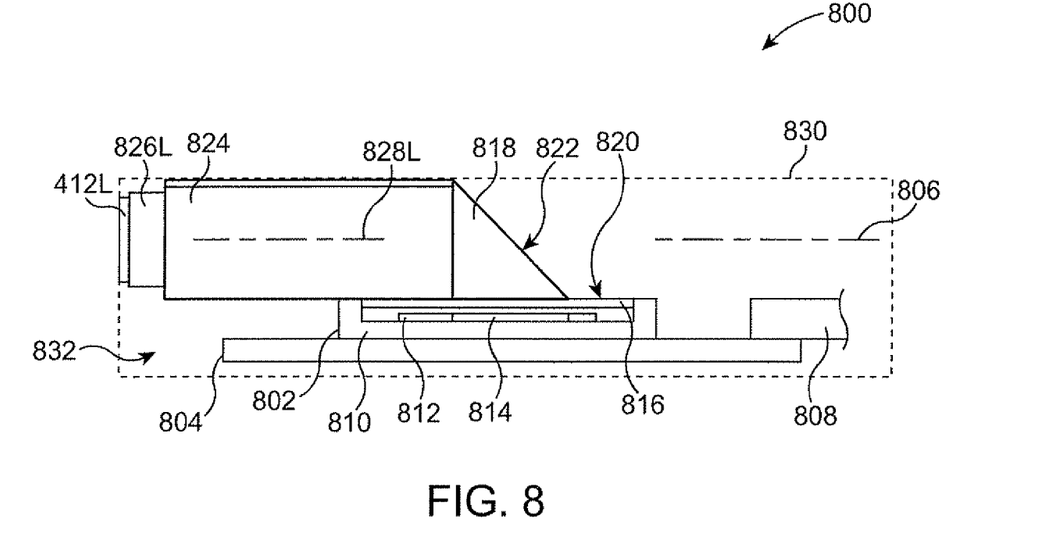
FIG. 8 is a cross-sectional schematic side elevation view of an image capture device.
Figure 9:
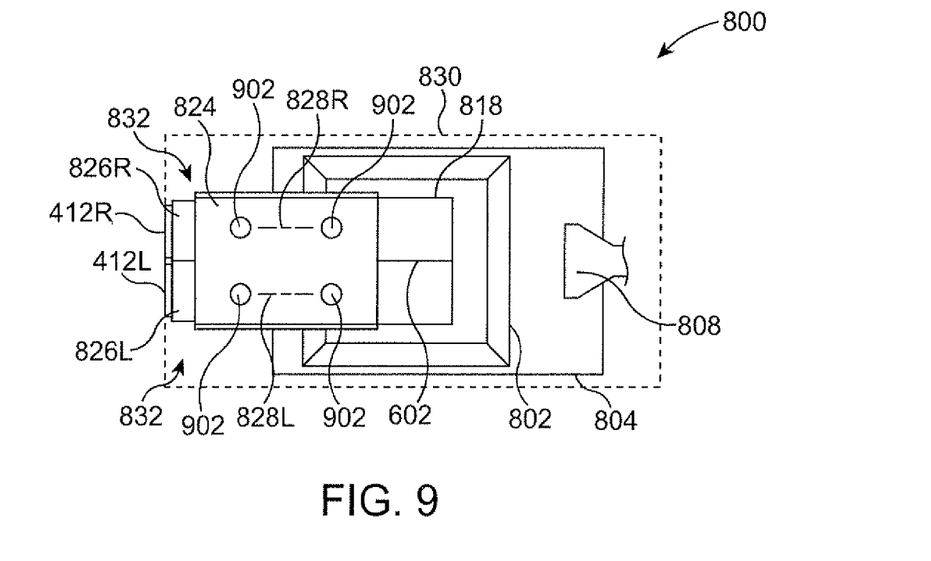
FIG. 9 is a schematic plan view of an image capture device.

FIG. 8 is a cross-sectional side elevation schematic view of an embodiment of image capture device 800. FIG. 9 is a schematic plan view of an embodiment of image capture device 800. Image capture device 800 functions as an endoscope for, e.g., minimally invasive surgical procedures and is part of image capture subsystem 302.

As shown in FIGS. 8 and 9, an image capture integrated circuit 802 is positioned over and electrically coupled to printed circuit board 804. Image capture integrated circuit 802 and printed circuit board 804 are mounted in image capture device 800 so that they are substantially parallel to longitudinal axis 806 of image capture device 800. Cable 808 is also electrically coupled to printed circuit board 804. Printed circuit board 804 includes electronic components that support the transfer of captured image data from integrated circuit 802 via cable 808 to subsequent graphics processing operations, as described above. Components of image capture integrated circuit 802 include package 810, the semiconductor chip 812 that includes active image sensor array 814 (rows and columns of imaging pixels; the array generally defines the boundaries of image sensing area 100), and glass 816 positioned over image sensor array 814.

Optically clear right triangular prism 818 is mounted (e.g., glued) so that one side face is flush with top surface 820 of glass 816. An adhesive with an index of refraction matched to the prism and cover glass material may be used to prevent reflections from occurring at this interface. As described above with reference to FIGS. 5 and 6, side face 822 of prism 818 acts a reflective plane that reflects light exiting the stereoscopic optical lens trains onto image sensor array 814.

Since there is a slight gap between the top surface 820 of glass 816 and image sensor array 814, however, a small amount of right and left image light may cross over on the surface of sensor array 814 because the field separator in prism 818 does not extend to the surface of image sensor array 814. This cross over is illustrated as cross talk area 110 in FIG. 1. In other embodiments the field separator may be positioned closer to the image sensor array, thus further minimizing or eliminating the image cross over.

FIGS. 8 and 9 further show lens mount 824 that, in this illustrative embodiment, holds two lens tubes 826R and 826L, each containing a lens train, one (e.g., 402R) for the right side image and one (e.g., 402L) for the left side image, as described above. As shown in the FIGS. 8 and 9 embodiments, the longitudinal axes 828R and 828L of the lens tubes are substantially parallel with each other, with longitudinal axis 806 of image capture device 800, and with the plane of image sensor array 814. Windows 412R,412L are positioned in front of lens tubes 826, and an IR filter as described above (not shown) is positioned between the lens tubes 826 and prism 818. As described above, the lens tubes 826R and 826L act as field separators. In one embodiment a black epoxy is used to fill the gap between the end of lens tubes 826R,826L and the input at the IR filter or prism 818 to further act as a continuous field separator. Other gaps in the field separator from the windows 412R,412L to the image sensor array 814 may be similarly filled.

A housing, represented as dashed line 830, surrounds the optical and electronic components of image capture device 800. The one or more windows 412 are joined with housing 830 so as to protect the internal components of image capture device 800 from an external environment such as a surgical site, chemical sterilization conditions, or the interior of an autoclave. In one embodiment housing 830 is about 15 mm high, 15 mm wide, and 25 mm long. In another embodiment, housing 830 is about 5 mm high, 10 mm wide, and 20 mm long. In yet another embodiment, housing 830 is about 25 mm long and has a cylindrical cross section with an approximately 12 mm diameter, which will allow it to be compatible with the form factor of endoscopes used with the da Vinci® surgical robotic systems.

Depending on the shape of housing 830, spaces 832 next to and under lens mount 824 may exist. Other components, such as components used to illuminate an object being imaged (e.g., optical fibers piping light from a remote source, a light generating source), may be placed in these spaces 832.

As shown in FIG. 9, lens mount 824 includes several small ports 902 that allow glue to be applied to keep lens tubes 826R and 826L in place in lens mount 824. During one construction embodiment jigs hold one assembly of integrated circuit 802 and printed circuit board 804 near another assembly of lens mount 824 and prism 818. In one embodiment lens mount 824 has features for prism 818 alignment, and lens mount 824 and prism 818 are glued together.

To align and attach the two assemblies, a UV-cured glue with a matched index of refraction as described above is placed between prism 818 and glass 816, and then the jigs are adjusted so that prism 818 reflects the left and right images onto the surface of the underlying image sensor array in proper alignment. Then, the right and left lens tubes 826R,826L are moved along longitudinal axes 828R,828L within lens mount 824 so that the left and right images are properly focused on the surface of image sensor array 814. If adjustment of the optical elements or spacing is required to match the image magnification to the required degree, this adjustment is also done at the same time. When the left and right images are properly adjusted, glue (e.g., 5-minute cure time epoxy) is applied via ports 902 to hold the lens tubes 826R,826L in place. Once the glue is cured, any final adjustment of the image position and rotation can be made by moving the lens mount 824 and prism 818 assembly, and then UV light is applied to cure the UV-cured glue between prism 818 and glass 816. When the glues have cured, the assemblies are removed from the jigs and the right and left optical paths from the objective lens to the image sensor remain in alignment with proper focus.

Figure 10A:
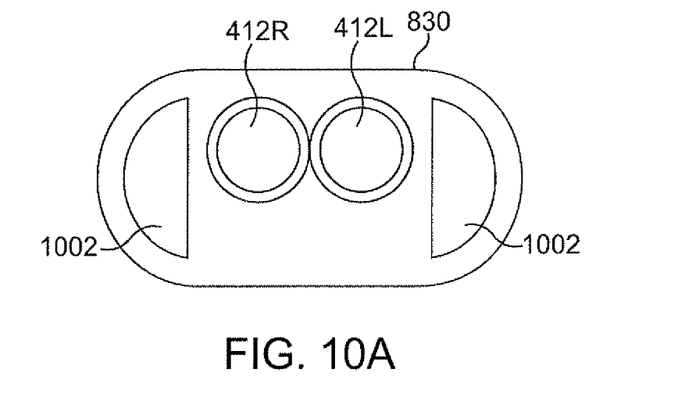
FIGS. 10A, 10B, and 10C are schematic front elevation views of an image capture device.
Figure 10B:
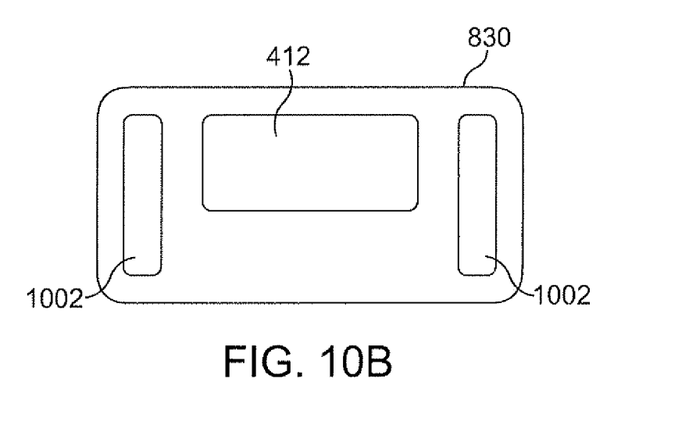
Figure 10C:
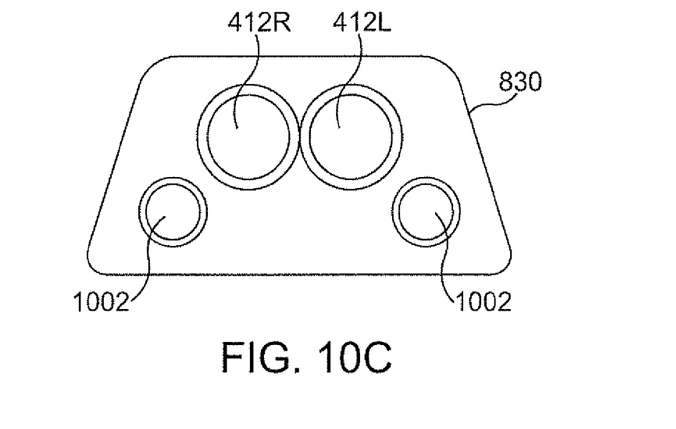

FIGS. 10A, 10B, and 10C are front schematic elevation views of device 800 that show windows 412, behind which lens tubes 826R,826L are positioned. FIGS. 10A-C illustrate various configurations and cross sections of housing 830, windows 412, and illumination ports. For example, FIG. 10A shows two D-shaped illumination ports 1002 positioned on either side of windows 412R,412L. Light to illuminate the object to be imaged is output through ports 1002. FIG. 10B shows a single window 412 used for both the right and left images, and also the illumination ports 1002 having a rounded rectangular shape. FIG. 10C shows circular illumination ports 1002. The shape and position of the one or more illumination ports 1002 shown in FIGS. 10A-C is illustrative of various configurations and arrangements of one or more illuminating structures. For example, the illumination port or ports may be positioned between the left and right optical trains. The illumination source may be inside housing 830 or may be separate from housing 830 and routed via, e.g., optical fiber.

Housing 830 may have various cross-sectional shapes. For example, FIG. 10A shows one illustrative embodiment of housing 830 having a rounded rectangle cross section. FIG. 10B illustrates housing 830 having another rounded rectangle cross section. FIG. 10C illustrates housing 830 having a rounded trapezoid cross-sectional shape. Other cross-sectional geometric shapes (e.g., regular and irregular polygons having rounded or sharp corners, continuous curves) may be used.

In one embodiment, the nominal working distance for lens trains 402R,402L is about 37 mm, and the depth of field is in the range from about 25-75 mm. In one embodiment, the field of view is about 60 degrees diagonally across the image area.

Figures 11A, 11B, 11C:
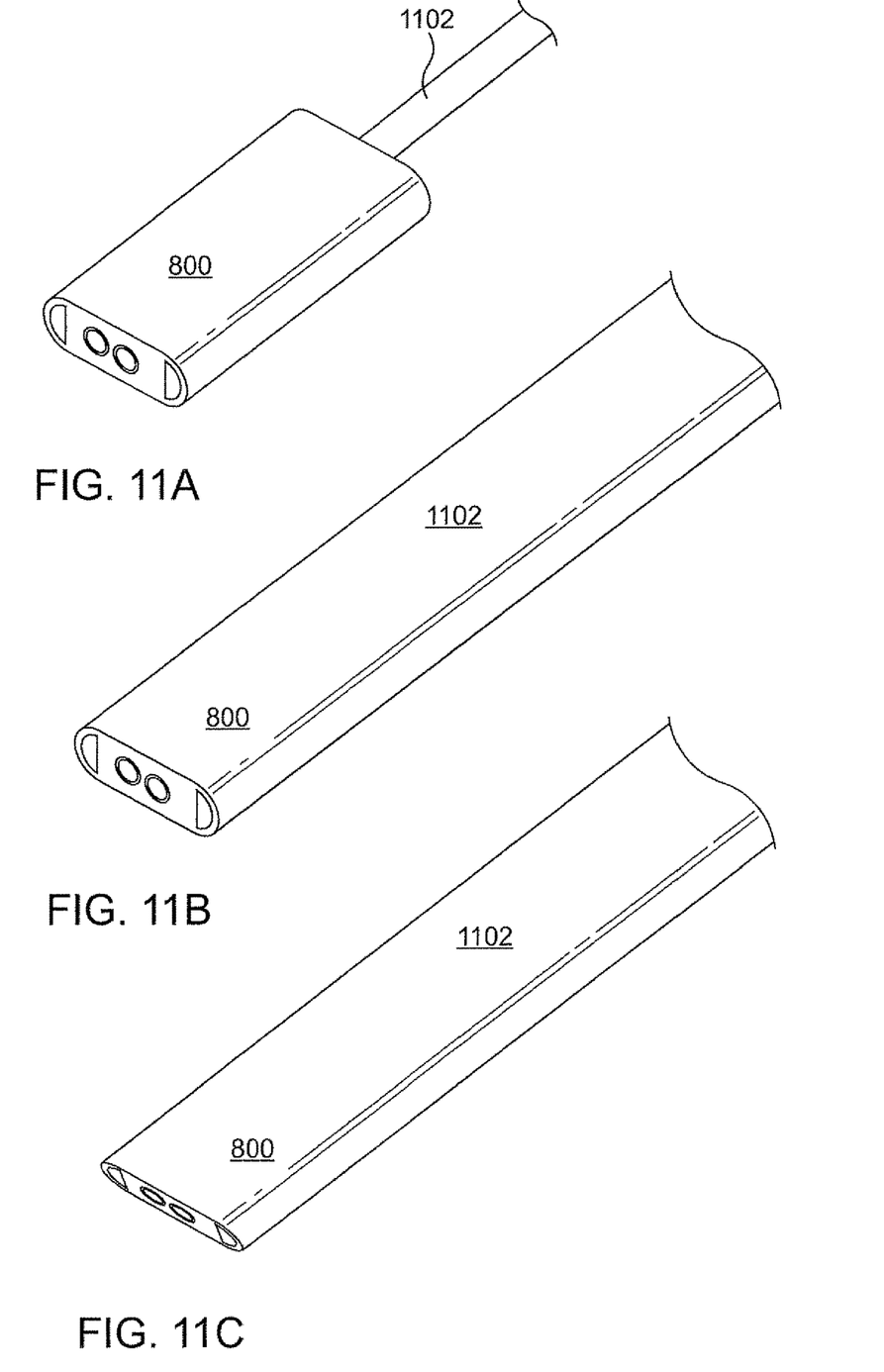
FIGS. 11A, 11B, and 11C are perspective views of an image capture device at the distal end of an endoscope.

FIGS. 11A-11C are illustrative perspective views showing various embodiments of image capture device 800 mounted at the distal end of an endoscope for use during minimally invasive surgery (e.g., robot-assisted surgery). The distal end is inserted, e.g., through a cannula, into a patient and is positioned to allow image capture device 800 to image a desired area in a surgical site. In FIG. 11A, endoscope body 1102 is shown having a cross section smaller than the cross section of image capture device 800. In one embodiment endoscope body 1102 is about 500 mm long and is about 5 mm in diameter or more. Endoscope body 1102 contains, e.g., power and data cables for the imaging components of image capture device and optical fibers for illumination. The distal end of endoscope body 1102 may be rigid, movable (discrete sections or continuum-type), or may have both a rigid and a movable portion. Various movement mechanisms are known for minimally invasive surgical applications. If the distal end is movable (the one or more joints are not shown), then in one embodiment endoscope body 1102 contains mechanical control components (e.g., actuation cables). Components (e.g., video data interface to image processing subsystem 304, electrical power connections, illumination connections, connections to motor actuators, etc.) associated with the features at the distal end of endoscope body are positioned at the proximal end (not shown) of endoscope body 1102. In one embodiment the outer covering of endoscope body 1102 protects the internal components from the surgical environment and from various sterilization methods.

FIG. 11B illustrates embodiments in which the cross-sectional shape of endoscope body 1102 is the same as the cross-sectional shape of image capture device 800. FIG. 11C illustrates embodiments in which image capture device is configured with optics that allow viewing at an angle (e.g., downwards), as described above. Although image capture device 800 is shown positioned at the distal end of an endoscope, in other embodiments image capture device may be mounted on other mechanisms used during surgery (e.g., used as a vision system for robots designed to move inside body cavities).

Referring to FIGS. 4, 5, 8, and 9, in one embodiment the inter-pupil distance between the left and right lens trains is about 2.4 mm, based on the use of the MT9M131 sensor. In another embodiment the inter-pupil distance is about 3.3 mm, based on stereoscopic considerations to match a given optimum working distance at the surgical site with the surgeon's perceived working distance at the stereoscopic display. Inter-pupil distance of the lens trains may be constrained by, e.g., the size of the sensor array or the size of the housing. Custom sensor designs, however, allow the designer to choose any value for the stereo separation rather than being constrained by the layout of a particular commercially available image sensor chip width.

Persons of skill in the art will understand that for optimum stereoscopic display, the ratio of the inter-pupil distance to the endoscope's working distance should be equal to the ratio of human inter-pupil distance to the perceived viewing distance in the fused display images. For example, for an average human inter-pupil distance of about 65 mm, a desired perceived viewing distance of about 18 inches (about 457 mm), and a desired 30 mm working distance of the endoscope, then the optimum inter-pupil distance for the left and right objective lenses is about 4.3 mm. In another exemplary embodiment, if the endoscope's desired working distance is about 37 mm, then the desired inter-pupil distance of the lenses is about 5.3 mm. Embodiments of the invention are constructed (e.g., using a custom image sensor array of sufficient width) to come as close as possible to a desired inter-pupil distance of the lens trains for specified endoscope working distances and perceived viewing distances and still stay within the size constraints specified for the image sensing device.

Figure 12:
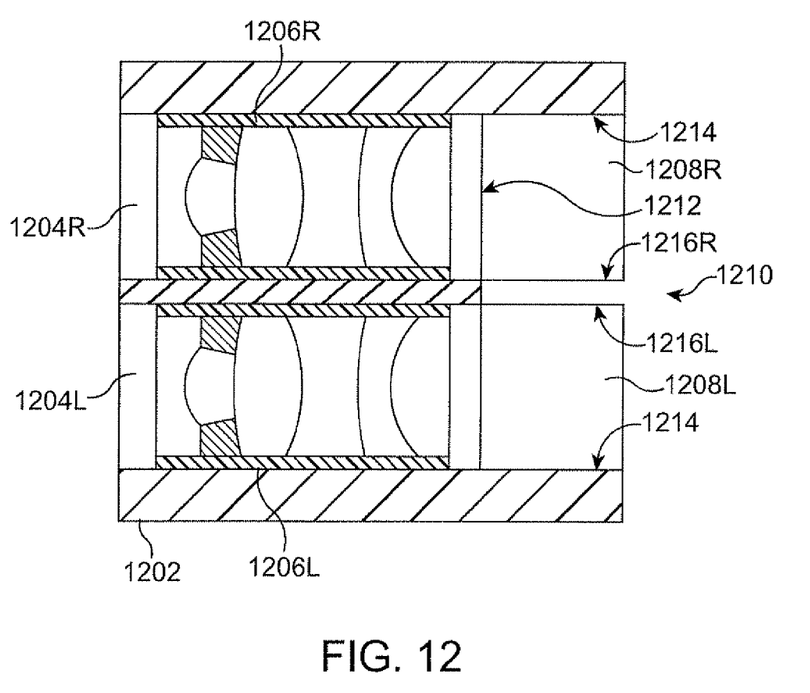
FIG. 12 is a schematic partial cutaway plan view of another embodiment of imaging optics.

FIG. 12 is a schematic partial cutaway plan view of another embodiment of imaging optics. In the embodiments illustrated by FIG. 12, two separate prisms are used to turn the right side and left side images onto the underlying image sensor area. The advantages of using a single prism are described above. Using two prisms, however, still retains some advantages such as the compact configuration of the optical path components and the underlying image sensor chip and the simplified alignment of the stereo images during assembly.

FIG. 12 shows lens mount 1202. Two channels 1204R and 1204L are aligned with lens mount 1202's longitudinal axis. In one instance channels 1204R,1204L are cylindrical, and other shapes may be used. Right lens tube 1206R slides in channel 1204R. Likewise, left lens tube 1206L slides in channel 1204L. As described above, sliding the lens tubes enables the image to be focused on the image sensing area. Other lens configurations, with or without sliding tubes, may be used. After the right and left side images are focused, the lens tubes are fixed in position within the channels as, e.g., described above. The shape of lens mount 1202 shown in FIG. 12 is illustrative of many variations.

Two reflecting prisms 1208R and 1208L are mounted within recess 1210 of lens mount 1202 such that the reflecting planes of each prism 1208R,1208L are substantially coplanar. In one embodiment the front faces of prisms 1208R,1208L are glued against back face 1212 of recess 1210 so as to be precisely aligned with the optical paths through lens tubes 1206R and 1206L. In addition, or alternatively, the prisms may be secured against side faces 1214 of recess 1210. Various suitable ways to mount the prisms may be used. Also, a single IR filter or two separate IR filters—one each for the right and left sides (not shown)—may be positioned between the prisms 1208R,1208L and lens mount 1202 or at some other suitable location in the right and left optical paths. The embodiment shown in FIG. 12 is illustrative also of one way in which one single prism that turns both right side and left side images, as described above, may be mounted.

Depending on the geometry of certain embodiments, the internal reflection of the inner end faces 1216R,1216L of prisms 1208R,1208L may be sufficient to keep light from one optical path from reaching the image sensing area for the other optical path. Other ways of separating the optical fields may be used, such as placing a non-reflective coating on end faces 1216R,1216L, placing a field separating piece between prisms 1208R,1208L, or extending a piece of lens mount 1202 between prisms 1208R,1208L.

FIG. 12 is illustrative of embodiments, such as those described above, in which the right side and left side images first come to focus at the surface of the image sensor. Other optical geometries are possible in which an image exists prior to the surface of the image sensor. In such embodiments, a field stop may be placed at the image point to prevent optical cross talk.

Alignment of the assembly that includes lens mount 1202, lens tubes 1206R,1206L, and prisms 1208R,1208L may be performed in a manner similar to the one described above. The precise mounting geometry of lens mount 1202 allows prisms 1208R,1208L to be set in position against it for subsequent alignment with the underlying image sensor area. That is, once mounted the prisms 1208R,1208L lose their individual degrees of freedom and may be treated as a single prism for alignment with the image sensor. Once alignment is complete, the lens and prism assembly is fixed to the optical sensor.

Figure 13:
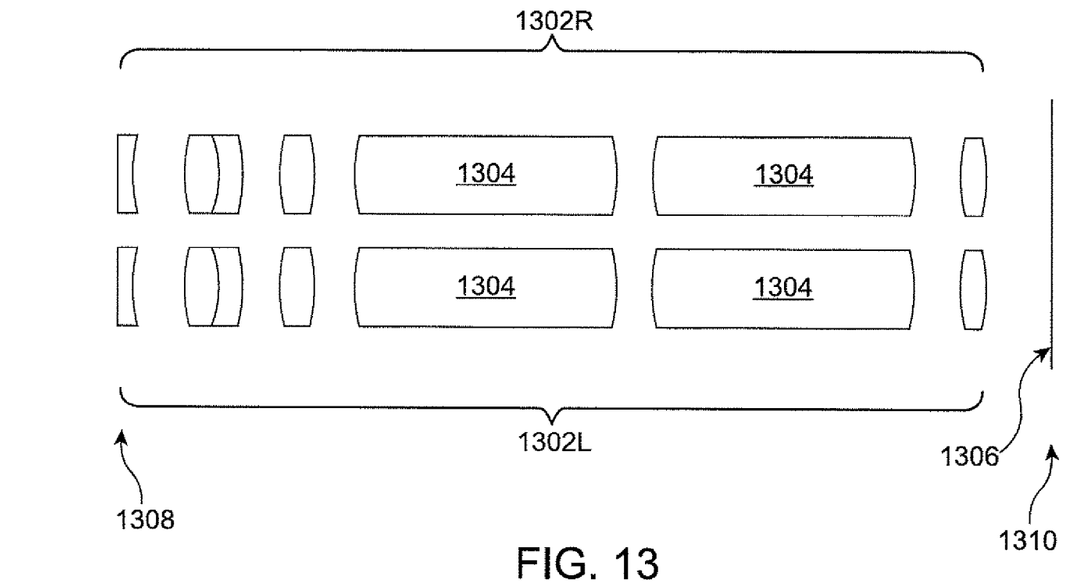
FIG. 13 is a schematic plan view of a relay lens and image sensor configuration.

As described above, various optical configurations may be used. FIG. 13 is a schematic plan view of a relay lens system in accordance with the invention. Light for the right side image is transmitted via right lens train 1302R, and light for the left side image is transmitted via left lens train 1302L. Each lens train 1302R,1302L is shown with two illustrative rod lenses 1304 in addition to other lenses. The right and left side images are focused on the surface of image sensing array 1306 (e.g., a 16:9 (1920×1080 pixels) width:height aspect ratio image sensor). As described above, the lens trains 1302R,1302L are spaced apart to provide a desired interpupillary distance within the constraints of the width of the image sensing chip that receives the right side and left side images.

Since the right side and left side images come to a focus at various positions in the lens trains 1302R,1302L, a field stop may be positioned at any of these foci. Other optical components, such as aperture stops and various filter types, may be positioned at various points in the lens trains.

The optics shown in FIG. 13 are illustrative of many embodiments in which a single image sensor area is positioned at a location other than at the distal end 1308 of an endoscope. For example, the single image sensing array 1306 may be placed at a proximate end 1310 of an endoscope, outside the patient's body. Such placement offers the simplicity of the single-chip being placed to receive both right side and left side images without the need for any turns (reflections) in the optical path from the object to the image sensor, and may also allow the distal end 1308 of the endoscope to have a relatively smaller size because the image sensing chip 1306 and its supporting circuitry are not located at the distal end 1308 inside the patient.

What is claimed is:

1. A method for capturing stereoscopic images with an endoscope, the method comprising:
    transmitting light from an object in a field of view of the endoscope along a first path through a first lens train of the endoscope and then through a first portion of a non-rectangular prism of the endoscope to be incident on a left side image area of a continuous image sensor surface;
    transmitting light from the object along a second path through a second lens train of the endoscope and then through a second portion of the non-rectangular prism to be incident on a right-side image area of the continuous image sensor surface;
    while transmitting the light along the first path and through the first portion of the non-rectangular prism, blocking the light transmitted through the first portion of the non-rectangular prism from being incident on the right-side image area of the continuous image sensor surface; and
    while transmitting the light along the second path and through the second portion of the non-rectangular prism, blocking the light transmitted through the second portion of the non-rectangular prism from being incident on the left side image area of the continuous image sensor surface.

2. The method of claim 1,
    wherein the portion of the first path through the first lens train and the portion of the second path through the second lens train are substantially parallel to each other and to the continuous image sensor surface.

3. The method of claim 2, further comprising:
    reflecting the light transmitted along the first and second paths through the non-rectangular prism off a face of the non-rectangular prism before directing the light along the respective first and second paths to be incident on the continuous image sensor surface.

4. The method of claim 3, wherein the respective portions of the first and second paths after reflecting the light off the face of the non-rectangular prism are substantially perpendicular to the respective portions of the first and second paths prior to reflecting the light off the face of the non-rectangular prism.

5. The method of claim 1, further comprising:
    separating the light transmitted along the first path through the first lens train from the light transmitted along the second path through the second lens train.

6. The method of claim 1, further comprising:
    transmitting the light along the first path through a color balance filter positioned between an objective lens of the first lens train and the non-rectangular prism.

7. The method of claim 1, further comprising outputting image data from each of the right side and left side image areas of the continuous image sensor surface for display.

8. The method of claim 7, wherein the outputting of the image data from each of the right side and left side image areas is synchronized.

9. The method of claim 7, further comprising outputting the image data from each of the right side and left side areas of the continuous image sensor surface to a graphics processing system.

10. The method of claim 1, wherein:
    blocking the light transmitted along the first and second paths comprises blocking the light using a field separator positioned between the first portion of the non-rectangular prism and the second portion of the non-rectangular prism.

11. A method for capturing stereoscopic images with an endoscope, the method comprising:
    transmitting light for a left side image of an object through a first lens of the endoscope and then reflecting the light for the left side image off a first portion of a reflective planar surface to be incident on an image sensor integrated circuit of the endoscope;
    transmitting light for a right-side image of an object through a second lens of the endoscope and then reflecting the light for the right-side image off a second portion of the reflective planar surface to be incident on the image sensor integrated circuit;
    while reflecting the light for the left side image off the first portion of the reflective planar surface, blocking the light for the right-side image of the object from being incident on a left side image capture area of the image sensor integrated circuit; and
    while reflecting the light for the right-side image off the second portion of the reflective planar surface, blocking the light for the left side image of the object from being incident on a right-side image capture area of the image sensor integrated circuit,
    wherein the light for the left side image and the light for the right-side image are reflected off the same single reflective planar surface.

12. The method of claim 11, wherein blocking the light for the right side image of the object from being incident on a left side image capture area of the image sensor integrated circuit and blocking the light for the left side image of the object from being incident on a right side image capture area of the image sensor integrated circuit comprises using a field separator positioned between the first portion of the reflective planar surface and the second portion of the reflective planar surface to prevent at least a portion of the light for the right side image from being incident on the left side image capture area of the image sensor integrated circuit and to prevent at least a portion of the light for the left side image from being incident on the right side image capture area of the image sensor integrated circuit.

13. The method of claim 11,
    wherein the reflective planar surface is a face of a prism.

14. The method of claim 11,
    wherein the endoscope comprises a housing containing the image sensor integrated circuit, the first lens, the second lens, and the reflective planar surface; and
    wherein the method further comprises transmitting the light for the left side image and the light for the right side image from the object positioned exterior to the housing to an interior of the housing through one or more windows in the housing.

15. The method of claim 11,
wherein the light for the right side image and the light for the left side image are each incident on different portions of the same single image sensor integrated circuit.

16. The method of claim 11,
wherein the light for the right side image and the light for the left side image do not pass through a common lens while being transmitted from the object to the reflective planar surface.

17. The method of claim 11, further comprising outputting image data for each of the right side and left side images from the image sensor integrated circuit for display.

18. The method of claim 17, wherein the outputting of the image data for each of the right side and left side images from the image sensor integrated circuit is synchronized.

19. The method of claim 17, further comprising outputting the image data for each of the right side and left side images from the image sensor integrated circuit to a graphics processing system.

20. A method for capturing stereoscopic images with an endoscope, the method comprising:

transmitting light for a left side image of an object through a first lens of the endoscope and then reflecting the light for the left side image off a reflective face of a first reflective prism to be incident on a left side image area of an image sensor surface of the endoscope;

transmitting light for a right side image of an object through a second lens of the endoscope and then reflecting the light for the right side image off a reflective face of a second reflective prism to be incident on a right side image area of the image sensor surface, the image sensor surface being a single continuous image sensor surface comprising the left side image area and the right side image area; and separating the light for the left side image from the light for the right side image by a field separator positioned between at least a portion of the first reflective prism and a portion of the second reflective prism, wherein the reflective face of the first reflective prism and the reflective face of the second reflective prism are substantially coplanar.

* * * * *